(12) United States Patent
Holmes

(10) Patent No.: US 11,198,229 B2
(45) Date of Patent: *Dec. 14, 2021

(54) HAIR CLIPPERS WITH FLEXING ELECTRICALLY ADJUSTABLE BLADES

(71) Applicant: Lonnie Holmes, Coram, NY (US)

(72) Inventor: Lonnie Holmes, Coram, NY (US)

( * ) Notice: Subject to any disclaimer, the term of this patent is extended or adjusted under 35 U.S.C. 154(b) by 77 days.

This patent is subject to a terminal disclaimer.

(21) Appl. No.: 16/547,535

(22) Filed: Aug. 21, 2019

(65) Prior Publication Data

US 2020/0061855 A1    Feb. 27, 2020

Related U.S. Application Data

(60) Continuation of application No. 15/677,018, filed on Aug. 15, 2017, now Pat. No. 10,391,646, which is a continuation of application No. 14/622,554, filed on Feb. 13, 2015, now Pat. No. 9,731,424, which is a continuation-in-part of application No. 13/727,274, (Continued)

(51) Int. Cl.
| | | |
|---|---|---|
| *B26B 19/02* | (2006.01) | |
| *A61B 17/88* | (2006.01) | |
| *B25B 23/00* | (2006.01) | |
| *B25B 23/142* | (2006.01) | |
| *B26B 19/20* | (2006.01) | |
| *B26B 19/04* | (2006.01) | |

(Continued)

(52) U.S. Cl.
CPC .......... *B26B 19/02* (2013.01); *A61B 17/8875* (2013.01); *B25B 23/0042* (2013.01); *B25B 23/1427* (2013.01); *B26B 19/046* (2013.01); *B26B 19/20* (2013.01); *B26B 19/205* (2013.01); *A61B 2090/031* (2016.02); *A61N 1/3752* (2013.01); *Y10T 29/49826* (2015.01); *Y10T 29/49876* (2015.01)

(58) Field of Classification Search
CPC ..... B26B 19/02; B26B 19/048; B26B 19/063; B26B 19/205; B26B 19/046; B26B 19/20
USPC .......... D28/44–54; 30/43.7–43.92, 194–204, 30/208–220
See application file for complete search history.

(56) References Cited

U.S. PATENT DOCUMENTS 3,264,735 A * 8/1966 Du Charme ............ B26B 19/20
                                                                  30/201
3,280,456 A * 10/1966 Erickson et al. ..... B26B 19/205
                                                                  30/201

(Continued)

FOREIGN PATENT DOCUMENTS

EP          2095914 A2  *  9/2009  .......... B26B 19/048
KR   20100103616 A  *  9/2010  .......... B26B 19/048

(Continued)

*Primary Examiner* — Jason Daniel Prone
(74) *Attorney, Agent, or Firm* — Alfred M. Walker

(57) ABSTRACT

A flex clipper provides a feature to help the cutting blade set float more effortlessly by adjusting automatically to the contours of a client's head to prevent getting stuck and causing cuts and irritation to the scalp. The hair clippers preferably also uses a self-contained motor-driven adjustment mechanism to adjust the relative position of the stationary and reciprocating blades of a common type of blade set. Two momentary switches operable by the thumb of the hand holding the clipper afford a barber total automatic adjustment with the clipper itself in an on or off condition.

14 Claims, 11 Drawing Sheets

Related U.S. Application Data filed on Dec. 26, 2012, now Pat. No. 9,352,476, which is a division of application No. 12/592,537, filed on Nov. 24, 2009, now Pat. No. 8,341,846.

(60) Provisional application No. 61/117,434, filed on Nov. 24, 2008.

(51) Int. Cl.
  *A61B 90/00* (2016.01)
  *A61N 1/375* (2006.01)

(56) References Cited

U.S. PATENT DOCUMENTS

| | | | | |
|---|---|---|---|---|
| 3,287,805 A * | 11/1966 | Du Charme | B26B 19/20 | 30/202 |
| 3,648,370 A * | 3/1972 | Cercone | B26B 19/20 | 30/201 |
| 3,988,828 A * | 11/1976 | Geary | B26B 19/24 | 30/210 |
| 4,085,503 A * | 4/1978 | Beck | B26B 19/06 | 30/201 |
| 4,150,482 A * | 4/1979 | Beck | B26B 19/12 | 30/43.9 |
| 4,797,997 A * | 1/1989 | Packham | B26B 19/046 | 30/43.92 |
| 5,577,324 A * | 11/1996 | Tanaka | B26B 19/14 | 30/43.6 |
| 5,606,799 A * | 3/1997 | Melton | B26B 19/063 | 30/216 |
| 5,704,126 A * | 1/1998 | Franke | B26B 19/046 | 30/43.91 |
| 5,706,582 A * | 1/1998 | Hosokawa | B26B 19/046 | 30/43.92 |
| 6,226,870 B1 * | 5/2001 | Barish | B26B 19/14 | 30/43.6 |
| D456,950 S * | 5/2002 | Rizzuto, Jr. | D28/53 | |
| 6,530,150 B1 * | 3/2003 | Barish | B26B 19/14 | 30/34.2 |
| 6,536,116 B2 * | 3/2003 | Fung | B26B 19/063 | 30/199 |
| D495,092 S * | 8/2004 | Massee | D28/50 | |
| 6,913,606 B2 * | 7/2005 | Saitou | A45D 26/0023 | 606/131 |
| 6,968,623 B2 * | 11/2005 | Braun | B26B 19/20 | 30/201 |
| D516,245 S * | 2/2006 | Ohta | D28/49 | |
| 7,137,203 B2 * | 11/2006 | Bressler | B26B 19/40 | 30/41 |
| D534,689 S * | 1/2007 | Gross | D28/53 | |
| D539,475 S * | 3/2007 | Dingelstad | D28/50 | |
| D539,476 S * | 3/2007 | Dingelstad | D28/50 | |
| D539,477 S * | 3/2007 | Dingelstad | D28/50 | |
| D544,999 S * | 6/2007 | Prat-Pfister | D28/50 | |
| D545,000 S * | 6/2007 | Marquez | D28/53 | |
| 7,234,240 B2 * | 6/2007 | Peter | B26B 19/40 | 30/41.6 |
| 7,234,242 B2 * | 6/2007 | Yao | B26B 19/06 | 30/201 |
| D546,001 S * | 7/2007 | McLachlan | D28/50 | |
| D549,873 S * | 8/2007 | Prat-Pfister | D28/50 | |
| D563,599 S * | 3/2008 | Prat-Pfister | D28/50 | |
| D567,443 S * | 4/2008 | Giannini | D28/53 | |
| D577,864 S * | 9/2008 | Kitagawa | D28/53 | |
| D577,865 S * | 9/2008 | Long | D28/54 | |
| D601,301 S * | 9/2009 | Bao | D28/50 | |
| D604,013 S * | 11/2009 | Qiu | D28/50 | |
| 7,690,117 B2 * | 4/2010 | Rogatschnig | B26B 19/10 | 30/43.2 |
| D637,759 S * | 5/2011 | Byun | D28/50 | |
| 7,992,307 B2 * | 8/2011 | Smal | B26B 19/20 | 30/202 |
| D651,746 S * | 1/2012 | Prat-Pfister | D28/50 | |
| 8,089,227 B2 * | 1/2012 | Baertschi | A46B 15/0075 | 15/21.1 |
| D672,504 S * | 12/2012 | Lyles | D28/50 | |
| D675,379 S * | 1/2013 | Yoon | D28/54 | |
| 8,341,846 B1 * | 1/2013 | Holmes | B26B 19/205 | 30/200 |
| 8,393,082 B2 * | 3/2013 | Shimizu | B26B 19/14 | 30/43.6 |
| D693,060 S * | 11/2013 | Lyles | D28/50 | |
| D695,961 S * | 12/2013 | Prat-Pfister | D28/50 | |
| D695,962 S * | 12/2013 | Prat-Pfister | D28/50 | |
| D698,085 S * | 1/2014 | Yoon | D28/53 | |
| D699,893 S * | 2/2014 | Marut | D28/49 | |
| D700,997 S * | 3/2014 | Marut | D28/49 | |
| D717,492 S * | 11/2014 | Kulshreshtha | D28/53 | |
| D717,493 S * | 11/2014 | Kulshreshtha | D28/53 | |
| D722,199 S * | 2/2015 | Boulanger | D28/53 | |
| D737,514 S * | 8/2015 | Roland | D28/50 | |
| D737,515 S * | 8/2015 | Roland | D28/50 | |
| D737,516 S * | 8/2015 | Roland | D28/50 | |
| D738,042 S * | 9/2015 | Roland | D28/50 | |
| 9,216,513 B2 * | 12/2015 | Brada | B26B 19/14 | |
| D748,857 S * | 2/2016 | Boulanger | D28/50 | |
| D754,398 S * | 4/2016 | Shimizu | D28/54 | |
| D758,014 S * | 5/2016 | Smith | D28/50 | |
| 9,352,476 B1 * | 5/2016 | Holmes | B26B 19/205 | |
| D758,659 S * | 6/2016 | Smith | D28/50 | |
| D765,914 S * | 9/2016 | Khubani | D28/44.1 | |
| D765,982 S * | 9/2016 | Nichols | D4/102 | |
| 9,731,424 B1 * | 8/2017 | Holmes | B26B 19/02 | |
| 10,391,646 B2 * | 8/2019 | Holmes | B26B 19/063 | |
| 2003/0101589 A1 * | 6/2003 | Barish | B26B 19/14 | 30/43.6 |
| 2006/0143924 A1 * | 7/2006 | Mercurio | B26B 19/04 | 30/43.91 |
| 2007/0256302 A1 * | 11/2007 | Okabe | B26B 19/141 | 30/43.6 |
| 2008/0034591 A1 * | 2/2008 | Fung | B26B 19/02 | 30/43.92 |
| 2008/0295340 A1 * | 12/2008 | Carlucci | B26B 19/063 | 30/199 |
| 2008/0301948 A1 * | 12/2008 | Kostner | B26B 19/063 | 30/199 |
| 2010/0325892 A1 * | 12/2010 | Nuber | B26B 19/265 | 30/45 |
| 2011/0131812 A1 * | 6/2011 | Erndt | B26B 19/063 | 30/34.1 |
| 2013/0326881 A1 * | 12/2013 | Blatter | B26B 21/446 | 30/41 |
| 2016/0052153 A1 * | 2/2016 | Oosterhoff | B26B 19/146 | 30/43.6 |
| 2018/0085941 A1 * | 3/2018 | Krauss | B26B 19/386 | |

FOREIGN PATENT DOCUMENTS

| | | | | |
|---|---|---|---|---|
| WO | WO 2008020981 A2 * | 2/2008 | | B26B 19/048 |
| WO | WO 2009081301 A1 * | 7/2009 | | B26B 19/048 |

* cited by examiner

HAIR CLIPPERS WITH FLEXING ELECTRICALLY ADJUSTABLE BLADES

RELATED APPLICATIONS

This application is a continuation of application Ser. No. 15/677,018, filed Aug. 15, 2017, which application is a continuation of application Ser. No. 14/622,554 filed Feb. 13, 2015, now U.S. Pat. No. 9,731,424 issued Aug. 15, 2017, which '554 application is a continuation-in-part of application Ser. No. 13/727,274, filed on Dec. 26, 2012, now U.S. Pat. No. 9,352,476 issued May 31, 2016, which '274 application is a divisional of application Ser. No. 12/592,537, filed on Nov. 24, 2009, now U.S. Pat. No. 8,341,846 issued Jan. 1, 2013, which '018, '554, '274 and '537 applications are incorporated by reference herein. Applicant claims priority under 35 U.S.C. § 120 therefrom. Application Ser. No. 12/592,537 is based upon provisional application Ser. No. 61/117,434 filed Nov. 24, 2008, which application is also incorporated by reference herein. Applicant claims priority under 35 USC § 119(e) therefrom.

FIELD OF THE INVENTION

The present invention relates to hair cutting.

BACKGROUND OF THE INVENTION

Electrically operated hair clippers have peen used for many years. Some of the commonly available models have a manual lever on the side to incrementally adjust the relative position between the stationary and the reciprocating blades in a blade set to adjust the minimum length of hair that is being clipped. Other prior art patents show infinite adjustability over a range. The prior art does not reveal motor-powered continuous adjustability of the blade set which affords the barber the ability to perform the adjustment even during the clipping activity by simply activating a switch and/or having a flexing compliance blade set that adjusts around the contours of the scalp of a flex clipper is described which, in addition to the aforementioned powered hair cutting length adjustment feature, provides an additional feature to help the cutting blade set float more effortlessly by adjusting automatically to the contours of a client's head, to prevent the blade set getting stuck and causing cuts and irritation to the scalp of the customer.

OBJECTS OF THE INVENTION

It is therefore an object of the present invention to provide a flexing hair clipper with a flexing, cutting blade adjuster which adjusts automatically to the contours of a client's head to prevent the blade set getting stuck and causing cuts and irritation to the scalp.

It is also an object of the present invention to provide a hair clippers device with infinitely variable blade distances from the scalp of the patron.

Other objects which become apparent from the following description of the present invention.

SUMMARY OF THE INVENTION

The hair clippers of this invention use a self-contained motor-driven adjustment mechanism to adjust the relative position of the stationary and reciprocating blades of a common type of blade set, preferably with a flexing blade set to adjust to the contours of the scalp of the customer having his or her hair being cut and trimmed.

While other on/off switches can be used, preferably two momentary switches operable by the thumb of the hand holding the clipper afford a barber total automatic adjustment with the clipper itself in an on or off condition. There is no need for two-handed fidgeting or selection of only a few discrete increments of length adjustment as with the commonly available models. Since the small gear motors used for the adjustment are brush type or brushless permanent magnet motors winch are operated by direct current, the adjustment feature is most compatible with cordless clippers already using an on-board DC source in the form of a re-chargeable battery to drive the reciprocating blade. The invention will be described as a modification of a cordless clipper, although AC driven corded type clippers can also be modified with this feature by the addition of an on-board AC to DC power supply for the adjustment motor.

In the first embodiment, a modified blade set is used such that a gear rack is attached to the stationary blade. It is engaged with a worm gear pinion driven by a low speed gear motor through a reversible drive circuit. Either limit switches, limit sensors, or over-current sensors are used to disable the adjustment motor at either the long or short hair end limits. The motor then can only be driven in the opposite direction.

In the second embodiment, a conventional blade set is used. The modification is such that a motor-driven final gear replaces the manual handle thereby retaining the original mechanism (of any type) that is used to move the stationary blade relative to the reciprocating blade in the conventional blade set. A timing belt couples a rear mounted adjustment motor to a front side-mounted gear train coupled to the shaft of the blade shifting mechanism. Attached to the timing belt for linear back and forth excursions is a magnet with a pointer. The magnet is used to operate two normally closed magnetic reed switches placed at the opposite distal ends of the permissible excursion thereby serving the limit switch function. The pointer moves over a tri-colored linear scale viewable by the barber from the top of the hair clipper; this quickly indicates the hair length setting. A plastic housing cover over the adjustment motor at the back and over the timing belt and gear train at the side encloses the entire compact mechanism.

In a preferred third embodiment, a flex clipper is described which, in addition to the aforementioned powered hair cutting length adjustment feature, provides an additional feature to help the cutting blade set float more effortlessly, by adjusting automatically to the contours of a client's head to prevent getting stuck and causing outs and irritation to the scalp.

To achieve this automatic adjustment, the blade set with motor driven length adjuster in now housed in a separate module. Compliance is introduced between this module and the main housing of the flex clipper. The blade set can now tilt a small amount in any direction to automatically adjust to the local scalp contours while the cutting process is controlled as usual by grasping the main housing. The rigid attachment of the blade set to the housing is replaced by a flexing compliant attachment. Two methods are described, one is by using a large diameter short bellows while the other method uses a short length (a ring) of thick-walled elastomeric foam tubing which provides similar function.

Both flexing compliant attachments permit tilting and a small amount of linear axial movement between blade set and main housing, but both resist any relative rotational movement between blade set and main housing. This rotational resistance insures good control of the blade set by keeping the cutting edge always aligned with the top surface of the housing (as in a normal rigid attachment) except for any minor local tilting. This rotational stiffness must also resist the driving torque of the motor driving the reciprocating cutter blade.

Since the drive motor for the reciprocating cutter blade is in the main housing and the crank mechanism and blade set are in a separate module, a flexing compliant motor coupling that can follow any blade movements relative to the main housing is required. A metal bellows coupling of a diameter which fits inside the hollow interior of coupling bellows or foam ring is used. To keep the mass and size of the forward blade set module low, a modified cutting length adjuster mechanism is used; for example, in one embodiment, it uses a miniature stepper motor with a lead screw. The powering and control cable from the stepper motor driver in the main housing is also guided through the hollow interior of the coupling member.

The flexing compliance (i.e. spring characteristics) of the coupling member as well as the damping characteristics can be determined by the geometric design and material selected. The proper "feel" can be achieved through simulation and actual prototype testing known to those skilled in the art of hair clippers technology. While the damping characteristics are not as important as the compliance, they determine the smoothness and sound deadening performance. For the bellows, a wide variety of thermoplastic elastomers (TPE's) or rubbers can be used. By using thin material crossection, even normally rigid plastics such as nylons or polypropylene can be used. Geometric design of the bellows includes overall length and diameter as well as number and shape of convolutions. By using filled TPE's or alloys of rubber/TPE a wide variety of damping characteristics can be designed in. Foamed rubbers or TPE's can be used for a foam ring coupling; other parameters that can be selected include type of cell (open or closed) and size of the cells. Material selection must also pay attention to longevity and compatibility with lubricants and hair conditioners.

BRIEF DESCRIPTION OF THE DRAWINGS

The present invention can best be understood in connection with the accompanying drawings. It is noted that the invention is not limited to the precise embodiments shown in drawings, in which.

DETAILED DESCRIPTION OF THE INVENTION

Figure 1:
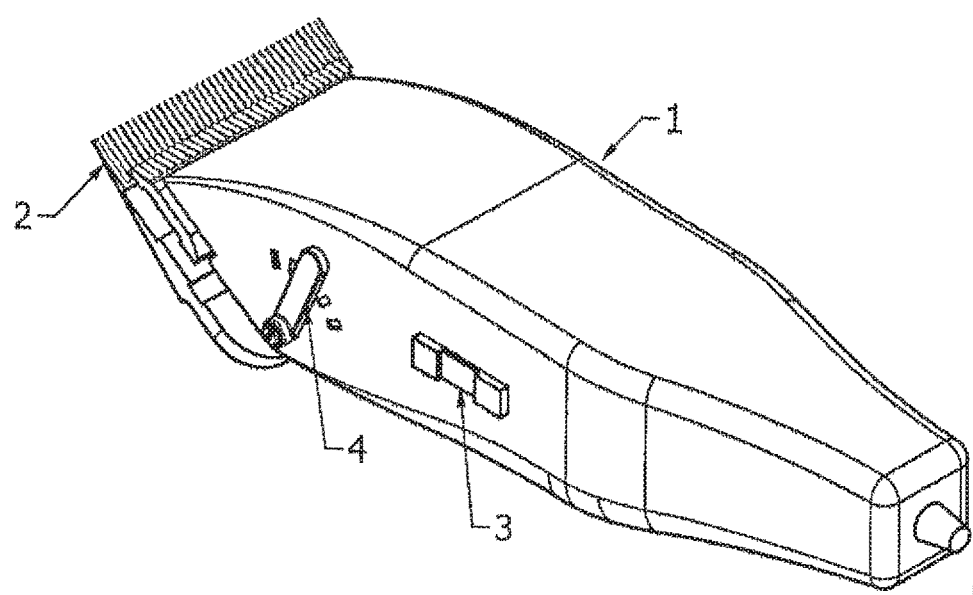
FIG. 1 is a perspective view of a typical prior art hair clipper with manual adjustment lever at the side.
Figure 2:
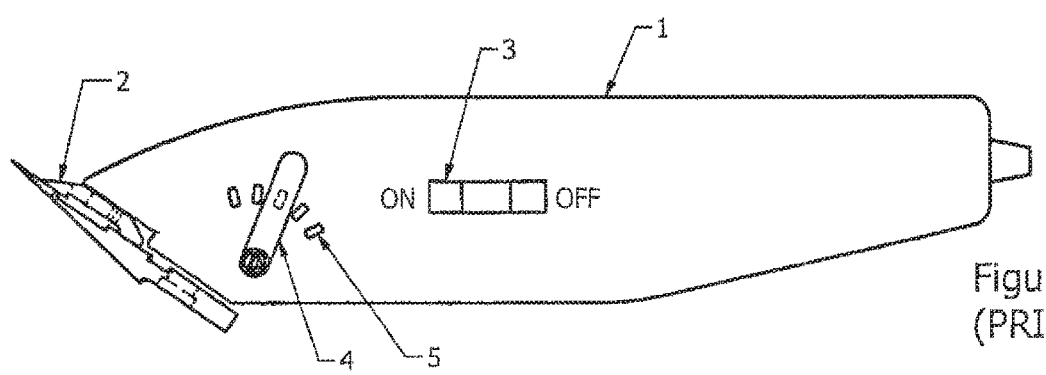
FIG. 2 is a side elevation of the prior art hair clippers of FIG. 1.

FIGS. 1 and 2 show two views of a conventional cordless electric hair clipper 1 with on/off switch 3, conventional blade set 2, and side manual incremental adjusting handle 4. The detents 5 engage handle 4 to set the minimum hair cutting length at one of the selections.

Figure 3:
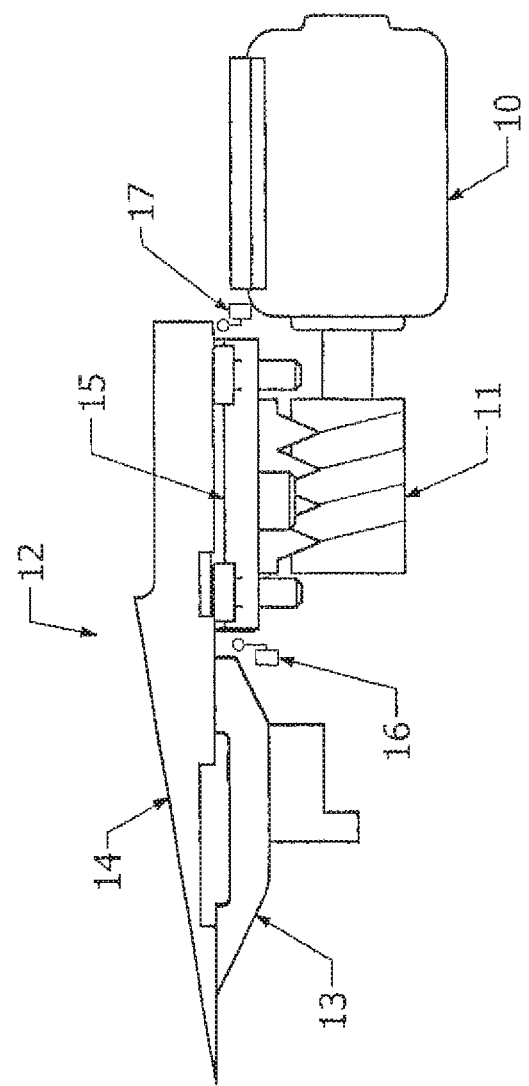
FIG. 3 is a side elevation of a motor-driven mechanism for adjusting the stationary blade of a clipper blade set showing a rack and worm gear pinion of the first embodiment.
Figure 4:
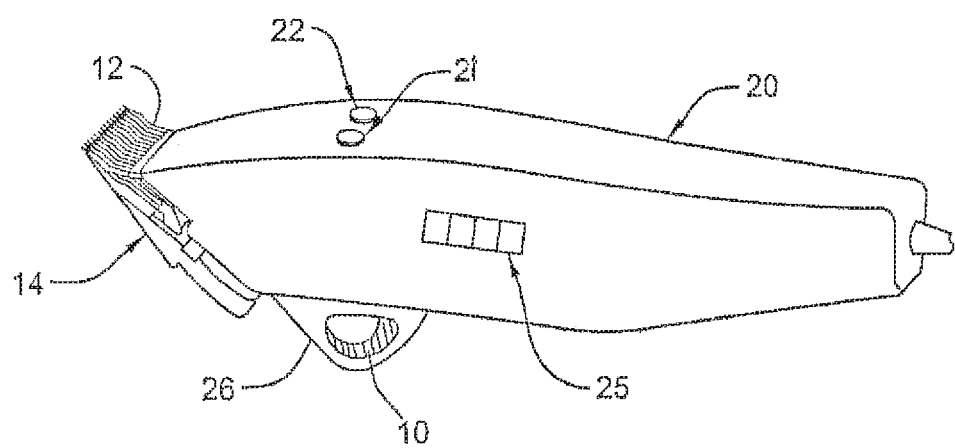
FIG. 4 is a perspective view of the hair clipper of this invention incorporating the mechanism of FIG. 3.
Figure 4A:
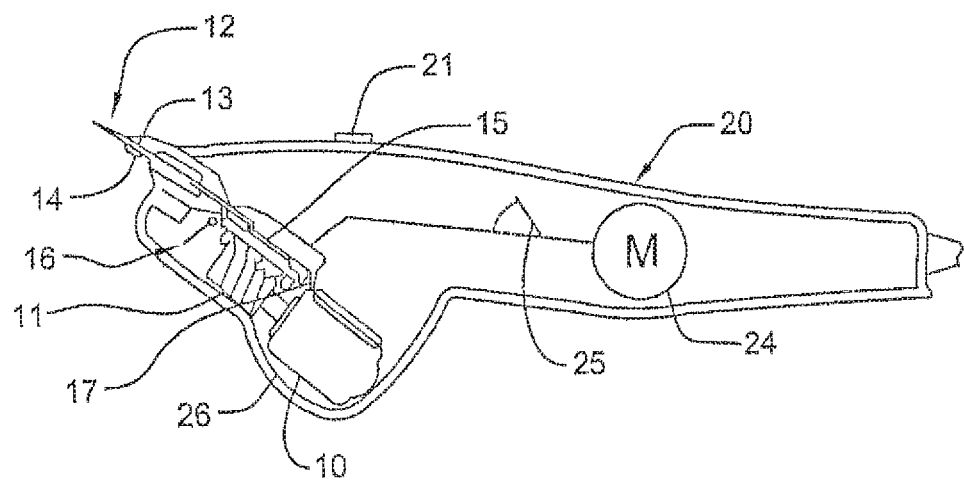
FIG. 4A is a side view in crossection of the hair clipper of this invention, showing the primary motor therein.

FIG. 3 shows the mechanism which uses gear motor 10 driving worm gear pinion 11 to perform an adjustment of stationary blade 14 relative to reciprocating blade 13 in blade set 12. A gear rack 15 subassembly is attached to, blade 14 and engages pinion 11. Also shown in this view are limit switches 16 and 17 at the longest and shortest settings respectively. FIGS. 4 and 4A show clipper housing 20 with the adjustment feature. Conventional on/off switch 25 connected to clipper motor 24 (shown schematically as an encircled "M") is at one side while momentary (or "tap") switches 21 and 22 on the top surface are used to energize gearmotor 10 in a direction toward longer settings or shorter settings respectively. Gearmotor 10 is enclosed in descending housing 26, which descends below clipper housing 20. While FIGS. 3, 4 and 4A show a worm gear, it is anticipated that other gears may be used, such as rack and pinion gears or other gears known to those skilled in the art.

Figure 5:
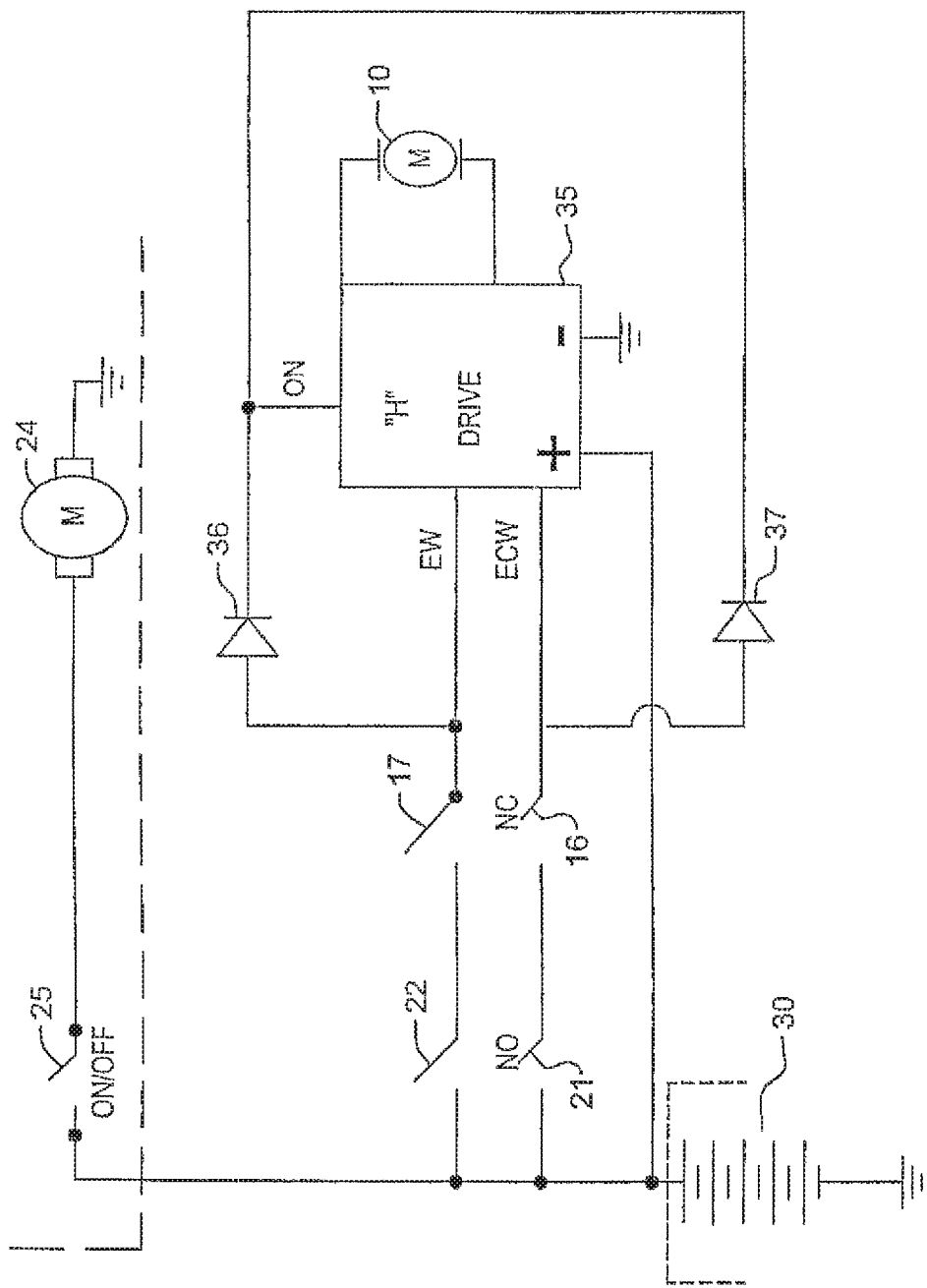
FIG. 5 is a wiring diagram of the adjustment motor using an "H-bridge" type of reversible driver.

FIG. 5 is a wiring diagram for the first embodiment of FIGS. 3 and 4 wherein gearmotor 10 is a simple brush type permanent magnet type driven by a common "H-bridge" drive module 35. Battery 30 is used primarily to power clipper motor 24 through on/off switch 25. It is also used as the power source for the adjustment feature. Drive module 35 has two direction inputs for clockwise and counter-clockwise operation, an "ON" input, and power input and motor output connections as shown. In operation, if normally open switch 22 is pushed, a signal will flow through normally closed limit switch 17 energizing the ON input through isolation diode 36; motor 10 will be driven clockwise until either switch 22 is released or limit switch 17 is opened at the end of the excursion. Similarly, if switch 21 is pushed, counter-clockwise operation is achieved through limit switch 16 and isolation diode 37. Once a limit switch is opened, motor 10 can only be driven in the opposite direction until the open limit switch is again closed.

Figure 6:
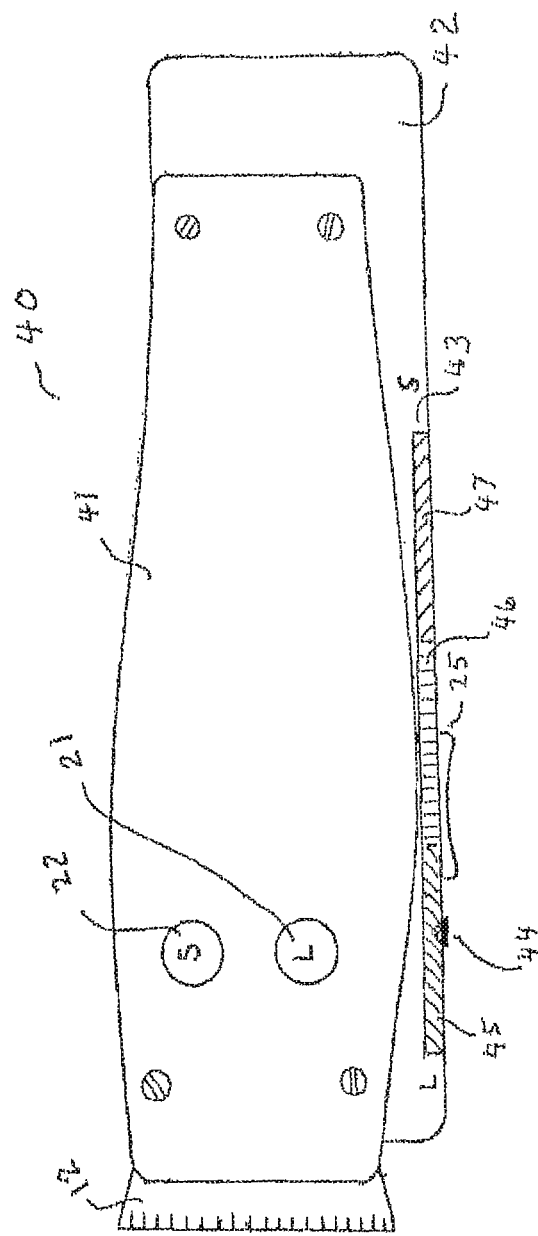
FIG. 6 is a top view of a second embodiment hair clipper with motor-driven adjustment of this invention.
Figure 7:
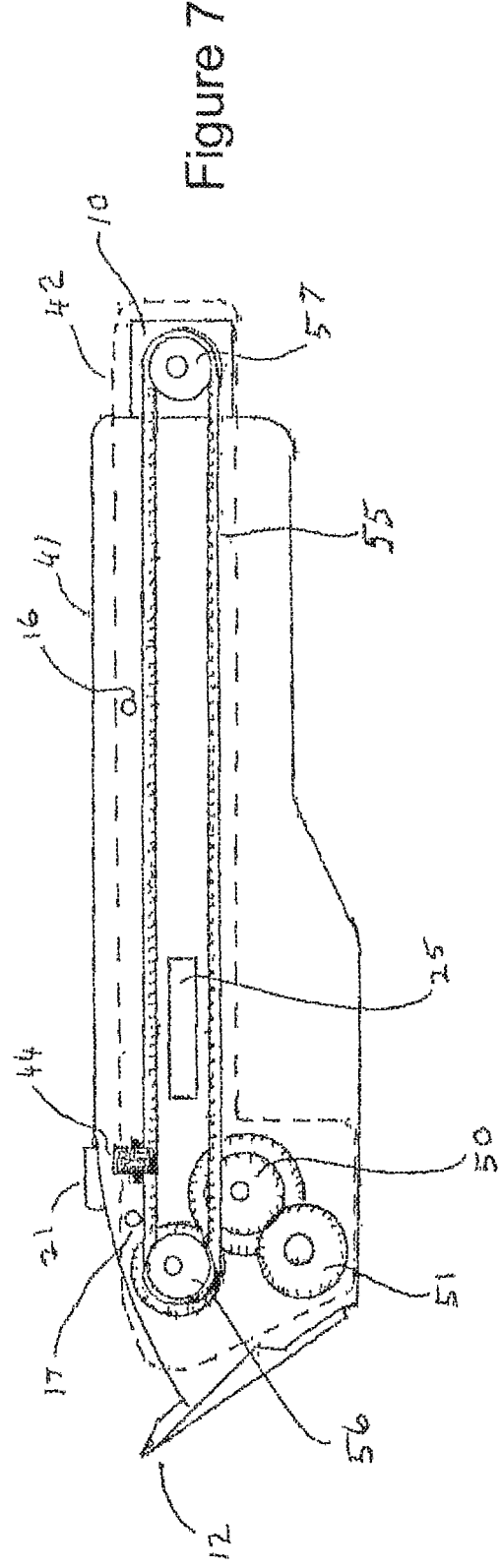
FIG. 7 is a side elevation of the second embodiment clipper with the housing cover removed to reveal the timing belt and gear train mechanism.

FIGS. 6 and 7 show top and side views of the second embodiment of motor-driven minimum hair length adjustable hair clippers. The same circuit shown in FIG. 5 is completely applicable to this embodiment as well. The same momentary ("tap") switches 21 and 22 are used to control motor 10 which is now placed at the back end of hair clipper 40. Except for the addition of switches 21 and 22, the housing 41 and internal mechanism is identical to that of the prior art cordless clipper shown in FIGS. 1 and 2. In this embodiment, a conventional blade set 12 and internal blade adjusting mechanism is used. The feature of this embodiment couples through the shaft formerly engaged with a manual handle 4. This is shown at the center of output gear 51. In the top view of FIG. 6, housing cover 42 is a plastic Shell used to enclose the feature mechanism. In FIG. 7, this cover 42 is removed to, reveal the mechanism; the position is shown in dashed lines. On the top edge of cover 42 is a tri-colored strip 43 with green region 45 denoting the long settings, yellow region 46 denoting medium length settings, and red region 47 denoting short settings. This scale is meant to be read relative to the position of pointer assembly 44 which is attached to timing belt 55 transmitting power and torque from pulley 57 mounted on motor 10 to pulley 56 attached to the input gear of gear train 50.

Gear train 50 is used to adjust the torque at output gear 51 and to match the speed and torque of gear motor 10 and the desired indicating excursion of belt 55 so as to form an ergonomic range. Besides the pointer on top, pointer assembly 44 also carries a small powerful magnet to operate limit switches 16 and 17 which are now implemented as normally closed magnetic reed switches. On/off switch 25 fits between timing belt 55 and pokes through a side switch hole in housing cover 42. While FIGS. 6 and 7 show a particular embodiment for an exterior mounted embodiment, it is anticipated that other exterior mounted embodiments may be used, such as those known to those skilled in the art.

While this third embodiment will be described as for a flex hair clipper with both powered hair cutting length adjustment as well as flexing compliance introduced between the main housing and blade set module, it should be noted that the flexing compliance feature to permit the blade set to automatically adjust to scalp contours and irregularities can be afforded to hair clippers without the powered hair cutting length adjustment. If the latter feature is not implemented, the blade set module will just contain the blade set and crank mechanism with coupling to the drive motor in the main housing which operates the reciprocating cutting blade; there would not be a cutting length adjuster motor, adjuster mechanism attached to the comb plate, nor a housing for the adjuster motor.

Figure 8:
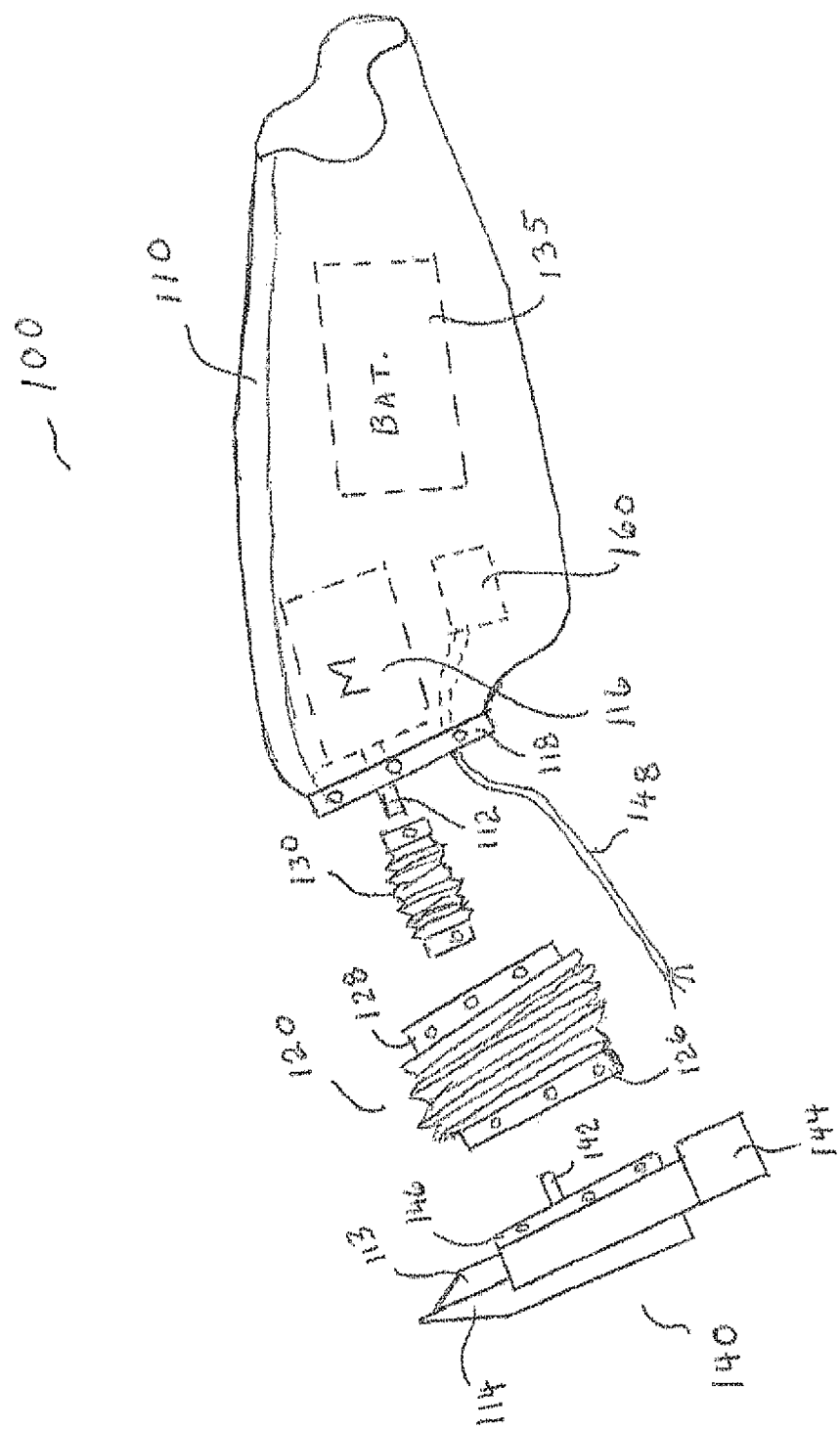
FIG. 8 is a side exploded elevation of the flex clipper embodiment of this invention.

FIG. 8 shows an exploded view of the major components of this embodiment. Flex clipper 100 has main housing 110 which contains drive motor 115 with shaft 112 which drives the reciprocating cutter blade 113, rechargeable battery 135 (unless it is an AC driven corded model), and an electronic driver module 160 for the hair cutting length adjuster motor 145 located in blade set module 140 at the left of the FIG. 8. Rigid coupling ring 118 is attached at the coupling end of housing 110. Blade set module 140 carries adjustable comb plate 114, reciprocating cutter blade 113, internal crank mechanism 143 for reciprocating cutter blade 113, drive shaft 142 for crank mechanism 143, housing 144 for internal hair length adjustment motor 145, internal hair length adjustment direct comb plate mechanism 114 (shown in FIG. 12), and a rigid coupling ring 146.

Also shown in FIG. 8 is molded compliant bellows 120 with integral mounting rings 126 and 128 is shown between blade module 140 and main housing 110, which it couples together. Metal bellows 130 couples drive motor 116 in main housing 110 and crank drive shaft 142 in blade module 140. Cable 148 powers and controls motor 145 for hair cutting length adjustment from electronic step driver module 160 contained in housing 144; it is passed through the hollow interior of bellows 120.

Figure 9:
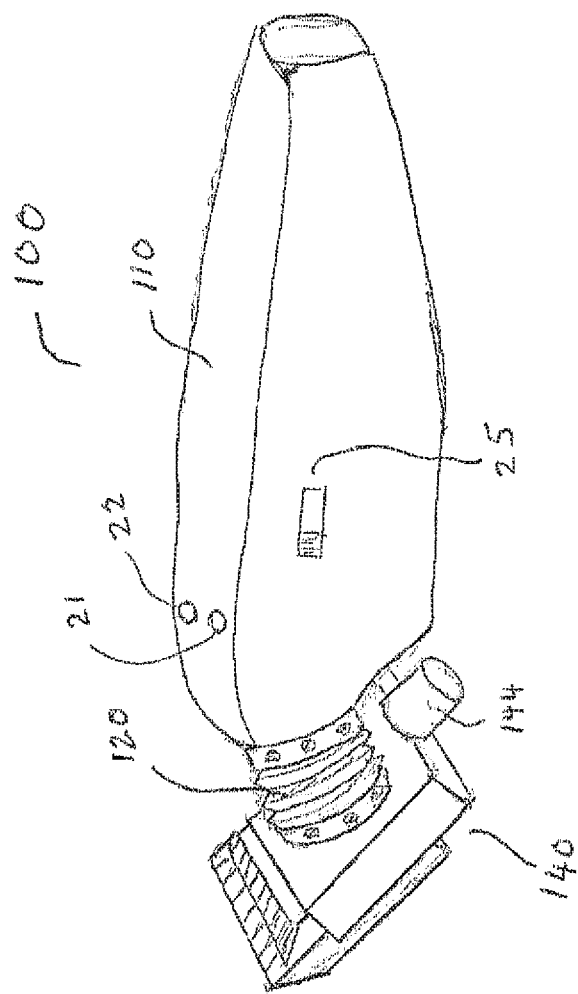
FIG. 9 is an assembled perspective view of the flex clipper of FIG. 8.
Figure 10:
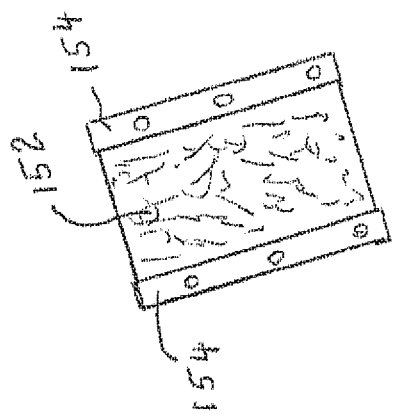
FIG. 10 is a side elevation of a compliant coupling between blade set module and main housing based on the use of an elastomeric foam ring.

FIG. 9 shows an assembled flex clipper 100 showing tap switches 21 and 22 for adjusting cutting length and clipper operating switch 25. A thumb operable reverse direction wheel 23 can also be optionally used. Bellows 120 is, shown coupling blade module 140 to housing 110 in a flexing compliant fashion. The length of bellows 120 as shown in FIGS. 8 and 9 may be shorter than shown based on the design and materials of the bellows. Bellows integral collars 126 and 120 fit over fixed collars 146 and 118 on blade module 140 and housing 110 respectively. Fasteners, such as self tapping screws, are used to secure the bellows collars to collars 146 and 118 which preferably have transverse holes in registration, FIG. 10 shows an alternate embodiment of an assembly 150 of resilient foam ring 152 with attached metal collars 154, which are adhesively attached or vulcanized as appropriate to the collar material. The assembly 150 of FIG. 10 can be used in lieu of custom molded bellows 120. Depending on many variables known to those skilled in the hair clippers technology, such as desirable product life, product price point, manufacturing cost, performance, volume, and materials used, either the bellows 120 or the foam ring assembly 150 may be the better choice.

Figure 11:
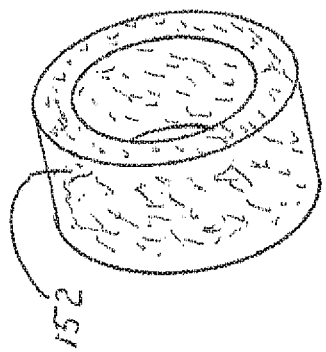
FIG. 11 is a perspective view of an elastomeric foam ring.

FIG. 11 shows a perspective view of the foam ring prior to attachment of coupling rings 154.

Although other types of flexing compliant motor couplings can be used, such as a variety of spring type couplings, the preferred coupling between shaft 112 and shaft 142 for reciprocating blade drive is a metal bellows coupling 130 such as those supplied by Servometer of Cedar Grove, N.J. This type of coupling easily fits inside the hollow bellows 120 or foam, ring 152 central hole while not interfering with the degrees of freedom of the bellows or foam ring.

Figure 12:
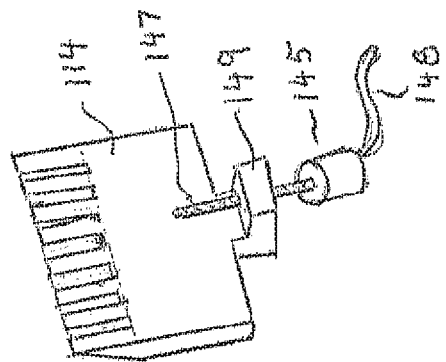
FIG. 12 is a perspective view of the cutting length adjuster mechanism as attached to the adjustable comb plate.

FIG. 12 shows the simple direct comb plate 114 adjustment mechanism which includes preferably stepper motor 145, and a fastening mechanism, such as, for example, threaded bracket 149 and fine lead screw 147. Although other methods can be incorporated, a stepper motor 145 is preferred to a DC gearmotor due to size and complexity. At about 6 mm diameter and 9.5 mm long, a FDM0620 stepper motor from Micromo of Clearwater, Fla. is very compact and is driven with 20 steps per revolution to drive lead screw 147.

Figure 13:
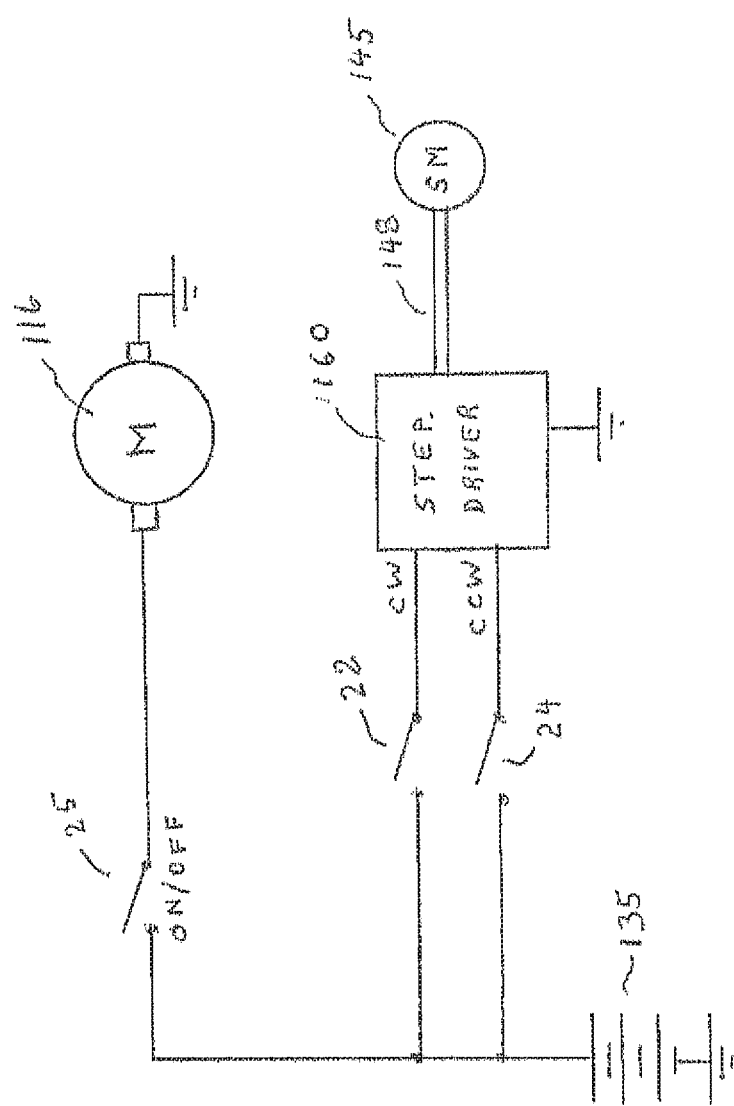
FIG. 13 is a high level schematic diagram of the electrical elements of the flex clipper of this invention.

FIG. 13 shows a schematic diagram for the flex clipper. It is noted that no limit switches are required because step motors can just "lose steps" with no damage when a hard stop is encountered. Tap switches 22 and 24 determine the direction of rotation of stepper motor 145 by supplying the proper sequence of steps from step driver module 160 over cable 148. Reciprocating blade motor 116 for reciprocating cutter blade 113 is directly powered through switch 25. Battery 135 (or equivalent DC power supply for corded versions) supplies power to both reciprocating blade motor 116, and to stepper motor 145, through step driver module 160.

In the foregoing description, certain terms and visual depictions are used to illustrate the preferred embodiment. However, no unnecessary limitations are to be construed by the terms used or illustrations depicted, beyond what is shown in the prior art, since the terms and illustrations are exemplary only, and are not meant to limit the scope of the present invention.

It is further known that other modifications may be made to the present invention, without departing the scope of the invention, as noted in the appended Claims.

I claim:
1. A flex hair clipper with both powered hair cutting length adjustment as well as flexing compliance, comprising:

a main hair clipper housing 110 having a reciprocating blade drive motor 116 driving a reciprocating cutter blade 113 and tap switches 21 and 22 located on said main hair clipper housing;

said reciprocating cutter blade 113 located within an exterior blade set module 140 located outside of said main hair clipper housing 110;

said reciprocating cutter blade 113 reciprocating in a direction transverse to an adjustable comb plate 114 which is adjacent thereto and also located within said exterior blade set module 140;

a power source being one of a battery 135 within said main hair clipper housing 110 and an AC driven corded power source;

said power source powering an electronic step driver circuit 160 within said main hair clipper housing 110, said electronic step driver circuit 160 being in communication with said tap switches, an adjustable stepper motor 145 located in said blade set module 140, said adjustable stepper motor 145 being in communication with said electronic step driver circuit 160 and in communication with said adjustable comb plate 114, wherein respective user manual manipulation of said tap switches allow for said electronic step driver circuit 160 to drive said adjustable stepper motor 145 which adjusts a position of said adjustable comb plate 114 relative to said driven reciprocating cutter blade 113;

said exterior blade set module 140 including said adjustable comb plate 114 and said reciprocating cutting blade 113 being located adjacent to each other and in the same plane; a flexible compliant coupling 120 connecting said main hair clipper housing 110 to said exterior blade set module 140;

said exterior blade set module 140 comprising said reciprocating cutting blade 113 and said adjustable comb plate 114 being flexibly coupled by said flexible compliant coupling 120 to said main hair clipper housing 110 for adjusting automatically to the contours of a client's head to reduce the possibility of said reciprocating cutting blade 113 and said adjustable comb plate 114 from getting stuck in respective hairs of a head of a client of the user of said flex hair clipper and to reduce the possibility of cuts and irritation to a respective scalp of the client of the user, said flexible compliant coupling 120 coupled to said exterior blade set module 140 and said main hair clipper housing permitting tilting and linear axial movement in any variable direction between said exterior blade set module 140 and said main hair clipper housing 110;

said flexible compliant coupling 120 resisting any relative rotational movement between said exterior blade set module 140 and said main hair clipper housing 110; wherein a resistance of said flexible compliant coupling 120 insuring control of said exterior blade set module 140 by keeping a cutting edge of said reciprocating cutting blade 113 aligned with a top surface of said main hair clipper housing 110 except for tilting;

said flexible compliant coupling 120 also rotationally resisting a driving torque of said reciprocating blade drive motor 116 driving said reciprocating cutter blade 113 adjacent to said adjustable comb plate 114 of said exterior blade set module 140; and, said reciprocating cutting blade 113 and said adjustable comb plate 114 in said exterior blade set module tilting a predetermined amount in any direction when contacting respective scalp contours while a user conducts a hair cutting process by the user grasping said main hair clipper housing 110.

2. The flex hair clipper as in claim 1 wherein said AC driven corded power source is AC power connected to said main hair clipper housing 110 via an electrical cord connected to an outlet of the AC power.

3. The flex hair clipper as in claim 1 wherein said battery power source 135 is rechargeable.

4. The flexing hair clipper as in claim 1 wherein a powering and control cable defines the communication between said electronic step driver module 160 in said main housing to said exterior blade set module 140 is guided through a hollow interior of said flexible compliant conduit 120.

5. The flexible hair clipper as in claim 1 wherein said flexible compliant coupling 120 is made of a thermoplastic elastomer (TPE).

6. The flexible hair clippers as in claim 5 wherein said thermoplastic elastomer (TPE) is a foamed elastomer.

7. The flexible hair clipper as in claim 1 wherein said flexible compliant coupling 120 is made of rubber.

8. The flexible hair clipper as in claim 7 wherein said rubber is foamed rubber.

9. The flexible hair clipper as in claim 1 wherein said flexible compliant coupling 120 is made of a plastic.

10. The flexible hair clipper as in claim 9 wherein said plastic is nylon.

11. The flexible hair clipper as in claim 9 wherein said plastic is polypropylene.

12. The flexible hair clipper as in claim 1 wherein said flexible compliant coupling 120 is made of an alloy of at least one thermoplastic elastomer and rubber, wherein a geometric shape of said flexible compliant coupling defines an overall length, diameter, and convolutions.

13. The flexible hair clipper as in claim 1 wherein said flexible compliant coupling 120 has a respective attachment collar 126 and 128 at each end of a pair of opposite ends thereof for attaching said flexible compliant coupling 120 to said main hair clipper housing and said exterior blade set module 140.

14. The flexible hair clipper as in claim 13 wherein said attachment collars 126 and 126 of said flexible compliant coupling 120 are attached to respective fixed collars 118 and 146 of said main hair clipper housing 110 and said exterior blade set module 140.

\* \* \* \* \*